United States Patent [19]

Stokoe, II

[11] Patent Number: 5,095,465
[45] Date of Patent: Mar. 10, 1992

[54] IN SITU TESTING WITH SURFACE SEISMIC WAVES OF MATERIALS HAVING PROPERTIES THAT CHANGE WITH TIME

[75] Inventor: Kenneth H. Stokoe, II, Austin, Tex.

[73] Assignee: Board of Regents The University of Texas System, Tex.

[21] Appl. No.: 462,404

[22] Filed: Jan. 5, 1990

[51] Int. Cl.$^5$ .............. G01V 1/00; G01N 29/04; G01H 3/02

[52] U.S. Cl. .............................. 367/14; 367/75; 73/598

[58] Field of Search ............. 367/14, 75; 73/573, 73/597, 598, 600, 602; 364/924.5, 421, 223.9

[56] References Cited

U.S. PATENT DOCUMENTS

| | | | |
|---|---|---|---|
| 4,372,163 | 2/1983 | Tithmann et al. | 73/602 |
| 4,703,460 | 10/1987 | Kurkjian et al. | 367/31 |
| 4,913,157 | 4/1990 | Pratt et al. | 73/597 |
| 4,926,070 | 5/1990 | Brandenburger | 73/597 |

OTHER PUBLICATIONS

Stokoe, K. et al., "In Situ Testing of Hard-to-Sample Soils", *Proceedings, Thirteenth Geotechnical Engineering Conference*, Turin, Italy, invited paper, Nov. 1987, 60 pp.
Nazarian, S. et al., "Near-Surface Profiling of Geotechnical Sties by Surface Wave Method", *56th Annual International Meeting of Society of Exploration Geopysicists*, Apr. 1986.
Nazarian, S. et al., "Application of Seismic Methods in Pavement Design and Analysis", Expanded Abstract, Society of Exploration Geophysicists, Nov. 1989.
Mok, Y. et al., "Use of Inverse Theory to Analyze Downhole Seismic Data", Expanded Abstract, Society of Exploration Geophysicists, Nov. 1989.
Rix, G. e al., "In Situ Testing of Landslide Debris in Valtellina, Italy Using Surface Waves", Expanded Abstract, Society of Exploration Geophysicists, May 1988.
Sanchez-Salinero, I. et al., "Analytical Evaluation of Variables Affecting Surface Wave Testing of Pavements", *Transportation Research Record* 1136, 1987.
Nazarian, S. et al., "Use of Surface Waves in Pavement Evaluation", *Transport Research Record* 1070, 1986.
Mok, Y. et al., "Analysis of Downhole Seismic Data Using Inverse Theory", *Proceedings, Ninth World Conference on Earthquake Engineering*, Tokyo, Japan, Apr. 1989, pp. 65-70.
Woods, R. et al., "Shallow Seismic Exploration in Soil Dynamics", *Proceedings, Richart Commemorative Lectures, Geotechnical Engineering Division*, ASCE, Oct. 1985.

(List continued on next page.)

*Primary Examiner*—Nelson Moskowitz
*Attorney, Agent, or Firm*—Arnold, White & Durkee

[57] ABSTRACT

An in situ method is disclosed for determining the structural integrity, set time and locations of anomalies or voids within a material as the material is being cured. Surface waves are transmitted and received a known distance along the surface of the material so that a substantially constant surface wave velocity can be calculated by dividing the known distance by the time it takes for the surface waves to travel the known distance. Surface wave velocity remains substantially constant for all wavelength measurements which do not exceed the thickness of the material. Structural integrity of the material, set time of the curing material and the detection of voids within the material can be determined from the substantially constant surface wave velocity. Structural integrity is determined as being proportional to the substantially constant surface wave velocity. Set time is determined from the slope or variation of substantially constant surface wave velocity plotted at various times during the curing process. Voids are determined as locations within the material causing surface wave velocity to change from substantially constant surface wave velocity to substantially non-constant surface wave velocity.

5 Claims, 5 Drawing Sheets

OTHER PUBLICATIONS sertation, The University of Texas at Austin (Dec. 1987).

Rix, G. et al., "Stiffness Profiling of Pavement Subgrades", *Transportation Research Record* 1235, 1990.

Stokoe, K. et al., "In Situ Seismic Testing with Surface Waves", *Proceedings Twelfth International Conference on Soil Mechanics and Foundation Engineering*, Rio de Janeiro, Brazil, vol. I, Balkema, Rotterdam, Aug. 1989, pp. 331-334.

Stokoe, K. et al., "In Situ Seismic Testing of Hard-to-Sample Soils by Surface Wave Method", *Proceedings*, American Society of Civil Engineers, Specialty Conference on Earthquake Engineering and Soil Dynamics II—Recent Advances in Ground Motion Evaluation, Park City, Utah, Jun. 1988.

Mok, Y. et al., "In Situ Damping Measurements by Crosshole Seismic Method", *Proceedings*, American Society of Civil Engineers, Specialty Conference on Earthquake Engineering and Soil Dynamics II—Recent Advances in Ground Motion Evaluation, Park City, Utah, Jun. 1988.

Nazarian, S. et al., "Determination of Pavement Layer Thicknesses by SASW Method", *Transportation Research Record* 1196, 1989.

Sheu, J. et al., "Effect of Reflected Waves on SASW Testing of Pavements", *Transporation Research Record* 1196, 1989.

Stokoe, K. et al., "Use of Rayleigh Waves in Liquefaction Studies", *Proceedings, Measurement and Use of Shear Wave Velocity for Evaluating Dynamic Soil Properties*, Geotechnical Engineering Division, ASCE, May 1985, pp. 1-17.

Nazarian, S. et al., "Nondestructively Delineating Changes in Modulus Profiles of Secondary Roads", *Transportation Research Record* 1136, 1987.

Sheu, J., "Applications and Limitations of the Spectral-Analysis-of-Surface-Waves Method", Ph.D. Dis-

IN SITU TESTING WITH SURFACE SEISMIC WAVES OF MATERIALS HAVING PROPERTIES THAT CHANGE WITH TIME

BACKGROUND OF THE INVENTION

This invention relates generally to a method for determining structural integrity of a material and for detecting subsurface voids within one or more layers of the material. More specifically, the present invention is directed towards using an easily determinable, substantially constant surface wave velocity as means for determining structural integrity, layer thickness, set time and subsurface anomalies within curing or cured materials. Substantially constant surface wave velocity can be measured in situ at different times during which the material is in the process of changing from a soft to hard state, or from a hard to soft state.

There has always been a need for determining the structural integrity of materials (i.e., asphalt, concrete, paint, glue, etc.) that change state or change density over time. Materials which are capable of being cured often exhibit different structural characteristics over time. Conventional structural tests are commonly done by taking representative samples of the material and applying compression force to the samples to determine the points in which the samples break. Samples are often withdrawn from the material after the material has cured or dried. A driver is applied to the sample and measurements are taken on how far the sample is compressed before it breaks or crumbles. The compression load and distance are then used to give the engineer an estimate of the strength of the sample. If the sample does not meet the engineer's specifications, the material is removed and a new material, hopefully within the engineer's specifications, will then be constructed.

The cylinder compression test requires that a sample be withdrawn from the material and that the sample be destroyed. Thus, a sample must be cut from the material and after the test is done, the area where the sample has been removed must be patched or filled-in. Often times, a sample is taken from a remote area so that the fill-in will not detrimentally affect heavily used, critical areas. For example, this is what occurs when highway engineers remove pavement samples from highway curbs or roadway edges rather than the middle of the highway. The problem with removing samples is that it takes time and a great deal of effort to cut the sample from the material body. In order to eliminate the time it takes to withdraw the sample, seperate samples are often made apart from the material itself. For example, a separate sample of concrete is often poured into test cylinders apart from the structure itself. Therefore, rather than removing a sample from a concrete pillar, a separate sample is poured and tested. However, the separately constructed samples are not always indicative of the material body itself. Concrete within large pillars can have inherently different characteristics than concrete in small test cylinders. Even if the cylinder sample and the pillar was poured at the same time, poured from the same "batch", or was on-site conditioned and cured under the same environmental conditions, smaller-mass test cylinders may not have the same structural integrity as does the larger-mass material (e.g., pillar). Therefore, testing of a sample of material cannot give the engineer a true and accurate measure of the material to which the engineer is really interested in measuring.

While cylinder tests analyze structural integrity of cured material, penetration resistance tests are used to analyze materials during the curing process. For example, penetration resistance of fresh concrete is the most common test used to determine to what extent the concrete has cured or has "set". Like cylinder tests, penetration resistance tests often require a sample of the material under test. A penetrometer is forced into the sample and the amount of force needed to cause 1 inch of penetration is recorded. The amount of force is then divided by the cross-sectional area of the penetrometer to calculate the penetration resistance. Initial set is defined as the time in which penetration resistance is equal to 500 lbs./sq. in (psi), wherein final set is when penetration resistance is 4000 psi. Set time is important in that it indicates the amount of curing taking place within the material, and the earliest time when it may be possible to make physical contact with the material.

Although set time can be tested prior to when the material being fully cured, structural integrity is typically tested not during, but after the material has cured. This requires that the material be hardened or stiff before the cylinder compression testing can begin. If the tests indicate poor structural integrity or a weakness within the sample, then the hardened material must be removed. Removing defective material after it becomes hardened can be very expensive when large amounts of cured material have been deposited.

In order to perform testing before the material has cured, seismic surface waves are typically used to predict subsurface properties. Spectral-Analysis-of-Surface-Waves (SASW) has been the preferred method used to predict subsurface properties. Although conventional SASW methods perform a non-intrusive, in situ testing upon the material either before or after curing is complete, conventional SASW methods can only predict a limited number of subsurface properties. Using a derived, substantially constant surface wave velocity, conventional SASW methods typically measure only Young's modulus or stiffness of the material. However, Young's modulus, in and of itself, is not an accurate indicator of the material's structural integrity, nor is Young's modulus an accurate predictor of set time. Moreover, Young's modulus cannot locate and identify subsurface anomalies or voids. While SASW can replace conventional cylinder compression and penetration resistance test as a preferred method of non-intrusively measuring Young's modulus, conventional SASW methods do not measure structural integrity (i.e., strength, or dampening properties of the material), set time layer thickness and, most importantly, cannot detect the presence of voids. Simply measuring Young's modulus will not provide the engineer with the more desirable measurements such as integrity, set time layer thickness and subsurface voids or anomalies.

SUMMARY OF THE INVENTION

Accordingly, it is desirable to provide a method for testing materials in situ during the time in which the material properties are changing (which can be either before or after the material has cured). For example, this invention allows one to test fresh concrete immediately after it is placed and before it has gained enough strength to allow one to walk on it. The concrete can be tested without having to withdraw a representative sample from the material or having to pour test cylinders. The present testing method performs the test in situ (i.e., at the actual material site) without having to withdraw a representative sample thereby leaving a void that must be filled-in later. Because testing is done on the material body itself, a more accurate indication of the material's properties can be measured. Also, the present invention does not destroy or intrude into the body of the material as required by conventional compression or penetration tests. Therefore, the test site can be tested and subsequently reused without having to patch or fill-in the test sample area.

In accordance with the instant invention, there is provided a device for nondestructive, seismic testing of four important aspects of materials: structural integrity, set time, thickness and the detection of voids in one or more layers of the material. Testing is performed by SASW methods on any type of material, or on "curing-type" materials that can be cured (hardened or softened) with the passage of time. More importantly, SASW determines all four aspects from a single, easily determinable, substantially constant surface wave velocity. At a specific time during the curing process, surface wave velocity is substantially constant for all surface wave frequencies having a wavelength less than the thickness of the material. Therefore, at each particular time during the drying process, a substantially constant surface wave velocity can be obtained, and from the substantially constant velocity, structural integrity, set time, thickness and subsurface anomalies can be measured. Structural integrity is proportional to the constant surface wave velocity, whereas detection of anomalies or voids cause surface velocity to be no longer substantially constant. Thickness is determinable at the surface wavelength in which surface wave velocity changes from a substantially constant to substantially non-constant velocity. Finally, set time is measured as the time in which penetration resistance exceeds a set amount. As time passes, the material becomes harder causing surface wave velocity to increase. This increase produces a surface wave velocity curve as a function of time, with a slope useable in calculating set time.

The present invention provides a method for determining structural integrity, set time, thickness and for detecting voids within curable or non-curable materials. The method involves transmitting and receiving surface waves traveling along the exposed surface of the material and measuring the travel time it takes for the surface waves to travel a known distance D along the exposed surface of the material. Once D is known and the travel time is determined, surface wave velocity can be calculated as a ratio of D divided by travel time. As long as wavelengths of the surface waves do not exceed the thickness of the material or layer of interest, surface wave velocity is substantially constant regardless of the fact that frequencies vary or that phase angle varies between the source and receiver or between receivers. Primarily because surface wave phase angle differences change in direct proportion to changes in surface wave frequency, surface wave velocity remains substantially constant over frequencies having wavelengths which do not exceed the material thickness.

In a preferred embodiment, the SASW method incorporates two or more receivers placed a distance D apart for measuring surface wave velocity between the receivers wherein each receiver is in contact with the exposed surface of the material. A surface wave generator is also contacted with the surface and spaced a known distance $d_1$ from the pair of receivers. Spacing between generator and receivers is adjustable in accordance with the wavelengths of the surface waves. Surface wave velocity is calculable from the ratio of the distance between receivers and surface wave travel time between receivers.

In another preferred embodiment, there are three or more receivers spaced known distances apart, wherein the known distance between adjacent pairs of receivers increase in proportion to the increasing distance between the receiver pairs and the surface wave generator. Thus, the further the receivers are located from the generator the larger the distance between receivers.

In still another preferred embodiment, there is only one receiver spaced a known distance from the surface wave generator. Surface wave velocity can be calculated from the travel time between the generator and the single receiver. There may be more than one surface wave generator depending upon the wavelengths being generated and the characteristics of the material being tested.

The present invention therefore provides an SASW method for measuring structural integrity, for detecting the presence of subsurface voids or anomalies, for determining the thicknesses of one or more surface or subsurface layers, and for determining set time of curing material. Measurements are made by an apparatus that can determine a substantially constant surface wave velocity residing within the curing or cured material. The SASW testing apparatus has one or more wave generators and one or more receivers seismically contacted with the exposed surface of the material. The generators produce seismic surface waves in response to electrical signals that can be either transient, periodic, random or steady-state signals. Conversely, the receivers produce electric signals in response to surface seismic waves transmitted through the material from the generators. Sufficient hardware is attached to the receivers so that the electrical signals can be analyzed and resultant material characteristics calculated. These and other advantages of the present invention will be further appreciated from the drawings and the detailed description provided below.

DETAILED DESCRIPTION OF THE PREFERRED EMBODIMENTS

The method used to perform an SASW test can be divided into three steps: (1) field testing, (2) dispersion calculations, and (3) calculation of material properties. In order to calculate characteristics of the curing or cured material, all three steps are needed. Field testing refers to the configuration of hardware and how that hardware extracts input data needed for dispersion calculations. Dispersion calculations are the transformations necessary to obtain surface wave velocity as a function of wavelength (i.e., dispersion curve). Finally, calculation of material properties involves the process of calculating structural integrity, presence of anomalies, layer thickness and set time within the material. The following sections describe each of these three steps in more detail.

Figure 1:
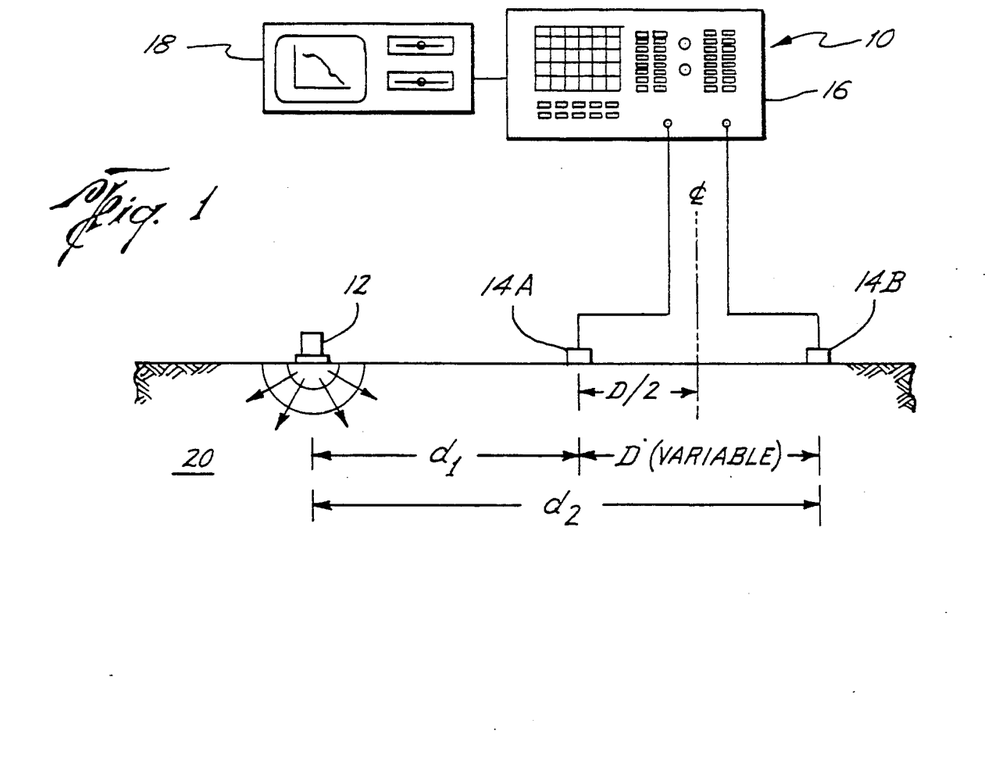
FIG. 1 is an apparatus capable of performing the SASW method of the present invention.

Referring to the drawings, FIG. 1 illustrates field testing setup 10 having a preferred embodiment of one signal generator 12, two receivers 14A and 14B, waveform analyzer 16 and micro computer 18. Generator 12 and first and second receivers 14A and 14B, respectively, seismically contact the upper surface of curing or cured material 20. Three types of generator 12 may be used to generate the required high-frequency waves. The first type is a mechanical, hammer-means capable of generating low frequency, seismic energy within material 20. For example, if material 20 consists of hardened portland cement concrete, mechanical hammer means can generate energy up to approximately 30 KHz. However, if material 20 is, for example asphalt concrete, mechanical hammers can generate approximately 20 KHz. A second type of generator, made of a ceramic piezoelectric or piezoelectric crystals, is capable of generating surface waves with much higher frequencies than mechanical hammers. Piezoelectric sources have a transducer which converts electrical energy to seismic energy by exciting a ceramic piezoelectric element mounted in a metal case and contacted with the exposed surface of material 20. Two suitable suppliers of piezoelectric transducers are: 1) "V" meters having appropriate output frequencies supplied by James Electronics, Inc., Model C4899 for the meter and Model C4898 for the transducer, and 2) Model F9 piezoelectric vibration generator with a matching network Model N9, and a power amplifier Model PATC, which can be purchased from Wilcoxon Research, Rockville, Mar. The third type of generator can be an electromagnetic vibrometer such as a 25 lb. shaker and matching power amplifier from MB Electronics. A suitable "V" meter with appropriate output acoustic frequencies, can be purchased from James Electronics, Inc., Model C4899 for the meter and Model C4898 for the transducer.

A piezoelectric source, such as the Wilcoxon F9, is more suitable than a mechanical hammer for generating high frequency surface waves needed for concrete or asphalt material 20. If generator 12 cannot produce high enough frequencies, noise becomes relatively large compared to the generated signal. The Wilcoxon F9 having a piezoelectric element is particularly suited for generating relatively high energy output over a wide range of frequencies. Also, a piezoelectric generator can generate many different types of input signals, including, but not limited to transient, periodic, random or steady state signals Because the Wilcoxon F9 piezoelectric produces a high energy output, first and second receivers 14A and 14B can be moved further from generator 12 without significantly lowering the signal detected by either receiver. Also, receiver 14B can be moved further from generator 12 and receiver 14A without jeopardizing its ability to detect surface wave signals transmitted from generator 12. Thus, the Wilcoxon F9 piezoelectric allow a larger area of material 20 to be sampled between source and receivers or between receivers. Substantial signal deterioration normally occurs in portland cement concrete when sampling distance exceeds approximately 4 feet. FIG. 1 shows $d_1$ as the distance between receiver 14B and generator 12. In its preferred, but not required configuration, receiver 14A is placed near the midway point between receiver 14B and generator 12. Depending upon the composition of the material being tested, receivers 14A and 14B can be moved either closer or further from generator 12. It is advantageous to keep receivers as far away from generator 12 as possible but not to far as to significantly decrease signal-to-noise ratio. The preferred distance $d_2$ between generator 12 and second receiver 14B is, for example, 6 to 24 inches in portland cement concrete applications, whereas preferred distance $d_1$ is preferably 3 to 12 inches. When general purpose tests are performed on materials other than curing concrete, $d_2$ can range from 0.5 ft. to over one hundred feet depending upon the wavelength (or frequency) transmitted by generator 12.

Receivers 14A and 14B detect surface waves transmitted along the surface of material 20 from generator 12. As receivers 14A and 14B detect the surface seismic waves, they convert seismic energy to electrical energy by means of accelerometers or velocity transducers contacted with the exposed surface of material 20. Accelerometers which exhibit suitable response to high-frequency (5 to 100 KHz) signals are manufactured by PCB Piezotronics, Inc., PCB Model 308B02 and Wilcoxon Research Model 728T or 736. If the surface of material 20 is relatively hard, receivers 14A and 14B, like generator 12, must be contacted with the surface by a mechanical means which can incorporate a "sticky" material such as glue, beeswax, etc. If material 20 has not yet cured, and the surface is not hard, generator 12 and receivers 14A and 14B are held against the surface by a controllable, mechanical means. Regardless of whether the surface is hard or soft, the contact points between generator/receivers and material must have seismic continuity so that the transmitted and received signals are accurate. Thus, the use of measuring devices which require no surface contact with material 20, such as laser vibrometers and detectors, are within the scope of this invention.

Electrical signals coming from receivers 14A and 14B are recorded in a waveform analyzer 16. Waveform analyzer 16 is a digital oscilloscope with the capability to perform waveform analysis and complex mathematical calculations such as Fast Fourier Transform in real time. A suitable instrument is Model 3562A manufactured by Hewlett-Packard. Fourier Transforms are needed to permit real time evaluations of the received wave signals and to store or record those signals so that they may be analyzed within the hardware provided within waveform analyzer 16. Portable micro computer 18 is connected to waveform analyzer 16 so that data can be retrieved from analyzer 16 and corresponding dispersion curves calculated. Also, micro computer 18 computes final values for structural integrity, detection of voids and set time of curing or cured material 20. Waveform analyzer 16 and micro computer 18 cooperate to perform tests and calculations rapidly so that the results are quickly available to the operator. A typical test, including equipment set up and data collection/analysis, may take less than several minutes to perform at each location. Micro computer 18 is obtainable from any commercially available personal computer manufactured used with any commercially available graphics program. Micro computer 18 is adaptable, through standard interface, to receive and transmit signals to and from waveform analyzer 16.

It will be understood that in accordance with the invention, different configurations of elements can be substituted into the preferred embodiment of FIG. 1 without deviating from the scope of this invention. First, any number of desired generators 12 and receivers 14A and 14B may be used to transmit and receive surface waves within material 20. Second, the method of contacting generator 12 or receiver 14A or 14B upon the surface of material 20 can vary depending upon the composition of material 20, generator 12 and receivers 14A and 14B. Third, waveform analyzer 16 can be any hardware apparatus that can do real-time analysis and storage of electrical signals while micro computer 18 can be any hardware apparatus that can perform all the calculations as described herein. Any type of computer capable of doing the computations described herein would be suitable, including a COMPAQ 386, MACINTOSH II, or IBM PC which are programmable with scientific applications programs that are particularly suited for this invention.

Dispersion calculations are normally taken from signal analysis of surface waves transmitted through material 20. Dispersion is the calculation of surface wave phase velocity or surface wave velocity as a function of surface wavelength or frequency of the surface waves as they travel from generator 12 to first and second receivers 14A and 14B, respectively. Given that the distances between generator 12 and receivers 14A and 14B are known, and that travel times within those known distances are determinable, the ratio of distance divided by travel time, i.e., surface wave phase velocity, can be calculated. The time delay between receivers 14A and 14B is a function of frequency and is expressed as:

$$t(f) = \theta_{yx}(f)/2\pi f$$

Phase angle $\theta_{yx}(f)$, is expressed in radians and frequency is in cycles/second. Once time delay, for each frequency $t(f)$ is known, surface wave phase velocity for that specific frequency $V_R(f)$, is determined using the following formula:

$$V_R(f) = (d_2 - d_1)/t(f)$$

FIG. 1 illustrates that $d_2 - d_1$ equals D wherein D is the distance between receivers 14A and 14B. If, however, only one receiver is used, then $V_R(f) = D_{gr}/t(f)$, wherein $D_{gr}$ is the distance between generator and receiver.

Once $V_R(f)$ is determined, then for purposes of computing the dispersion curve, wavelength can also be determined. Wavelength, or $L_R$, of the surface wave is calculated from:

$$L_R = V_R/f.$$

Figure 2:
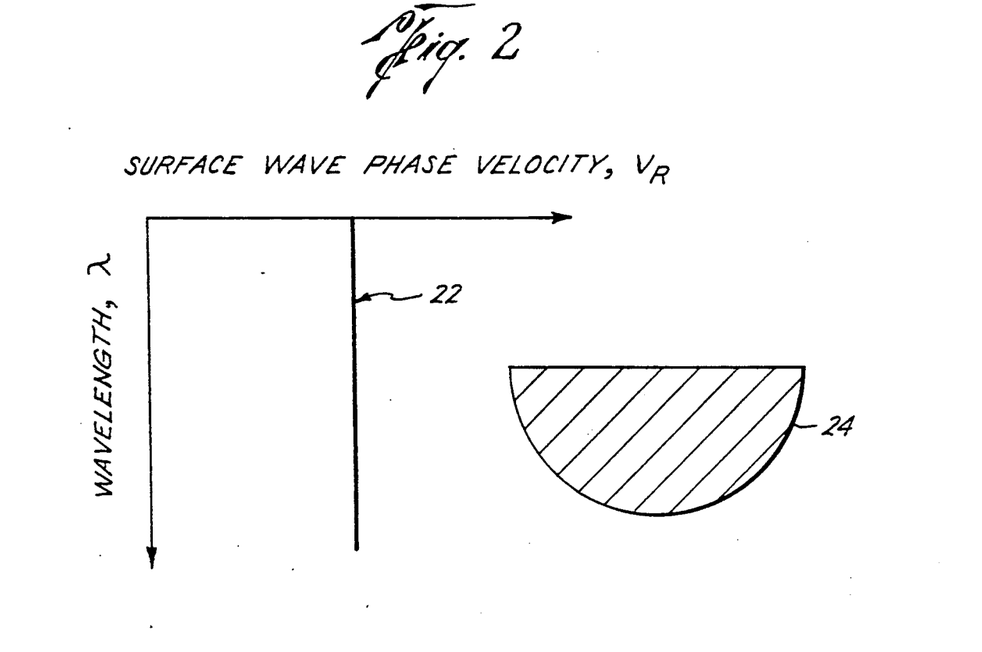
FIG. 2 is a graph illustrating surface wave phase velocity transmitted within a material having uniform composition.

All of the above calculations yield a dispersion curve wherein $V_R$ is plotted as a function of $L_R$. It is important to note that dispersion curve can also be expressed in terms of $V_R$ plotted as a function of $f$, however, $V_R$ plotted in terms of $L_R$ is the preferred method. Surface wave velocity, or $V_R$, is substantially constant within uniformly structured material 20. FIG. 2 illustrates a dispersion curve 22 having substantially constant surface wave phase velocity in a structurally uniform material 24. As long as the wavelength of the transmitted surface wave does not exceed the thickness of material 24, surface wave phase velocity will remain nearly constant in a structurally uniform material.

Figure 3A:
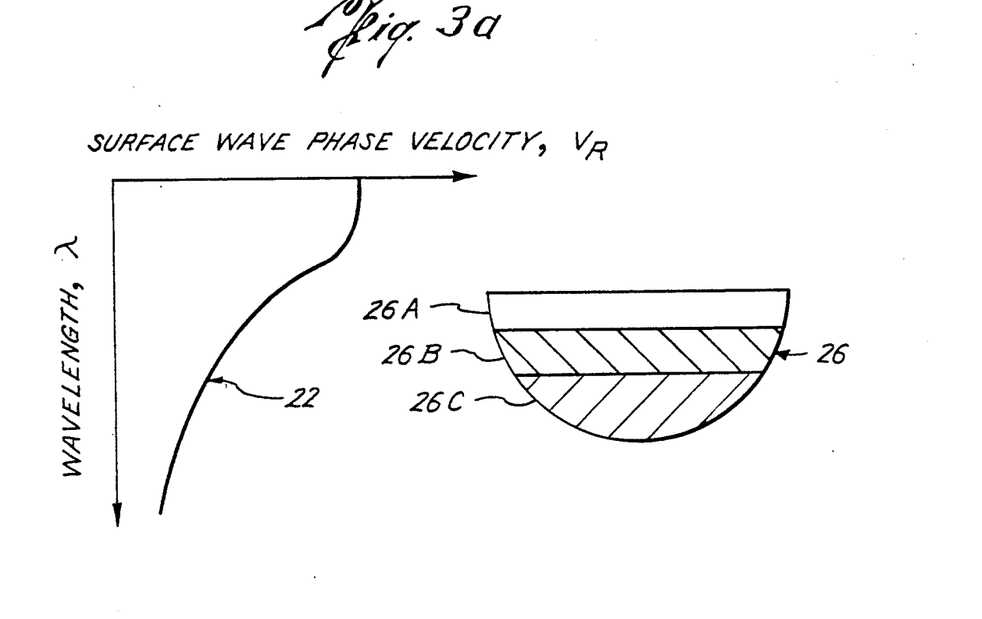
FIG. 3a is a graph of surface wave phase velocity transmitted through material having layers of different compositions.

FIG. 3a illustrates a dispersion curve 22, wherein surface wave phase velocity changes in a structurally non-uniform material 26. If layer 26A is stiffer than layer 26B and layer 26B is stiffer than layer 26C, surface wave velocity will decrease as wavelength increases. Conversely, surface wave velocity will increase as wavelength increases, if layer 26C is stiffer than 26B, and layer 26B is stiffer than 26A. Changes in dispersion curve 22 occur at the boundary between layers having differing stiffness. If the bottom layer is not as stiff as the top layer, surface wave phase velocity will decrease at the wavelength point corresponding to the measured thickness of the top layer. Thus, changes in surface wave phase velocity at specific wavelength points indicate the thickness of the surface layer in a material having two or more layers of different stiffness. Changes in surface wave velocity at the boundaries between non-uniform layers is caused by the fact that surface waves penetrate into hardened underlayers with increasingly greater shear and compression wave velocities. Since surface wave phase velocity is proportional to sheer and compression wave velocities of each of the layers, it is only normal that as shear and compression waves penetrate hardened underlayers, the surface wave velocity increases accordingly.

Figure 3B:
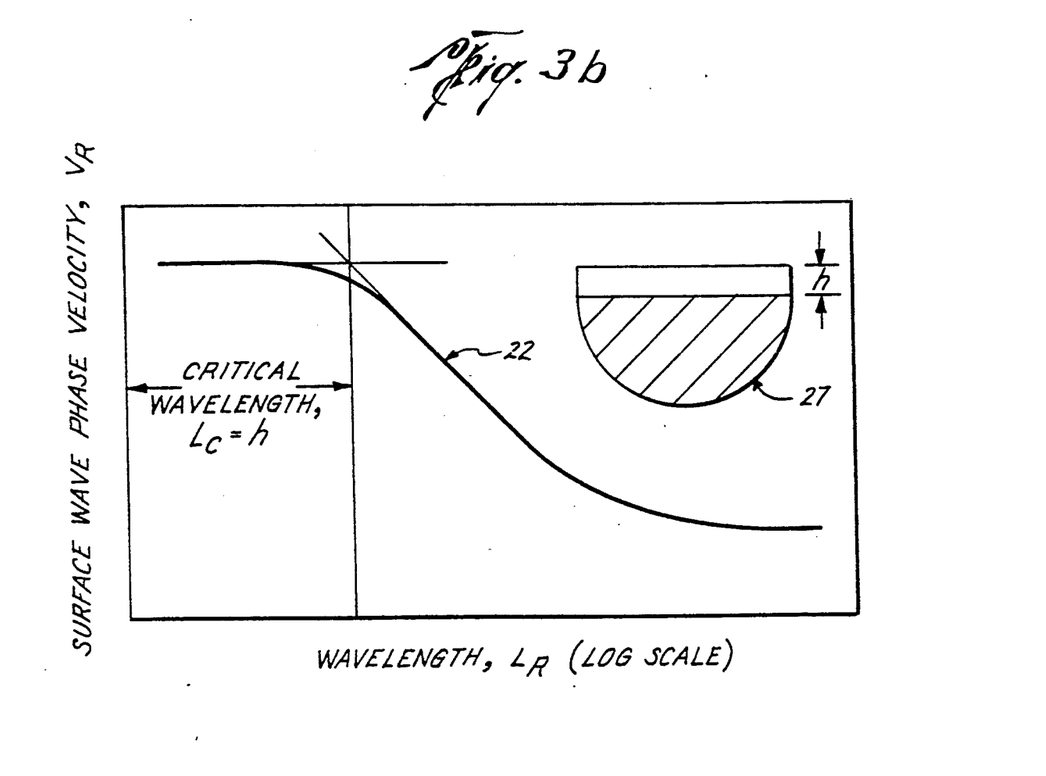
FIG. 3b is a graph of surface wave phase velocity changing from a substantially constant velocity to a substantially non-constant velocity at a critical wavelength corresponding to the thickness of the surface layer.

Referring to FIG. 3b, a dispersion curve 22 is shown in a structurally non-uniform material 27. Dispersion curve 22 indicates a change from a substantially constant surface wave phase velocity to a substantially non-constant surface wave phase velocity at a critical wavelength point equal to the thickness, h of a surface layer of structurally non-uniform material 27. Critical wavelength, $L_c$, provides a reasonably accurate measurement of the surface layer in situ, i.e., without having to bore into the surface and subsurface layers in order to visually measure thickness of the surface layer. Critical wavelength, $L_c$, can be visually obtained from waveform analyzer 16, or it can be digitally displayed upon micro computer 18. By periodically generating surface wave within the material to be tested, and passing testing set up 10 over the surface, areas having abnormal thicknesses can be detected. Once those areas are detected, curing material can be removed before it hardens. Thus, the present testing set up 10 can measure thicknesses at various points beneath the generators and receivers which scan over the surface layer.

Figure 4A:
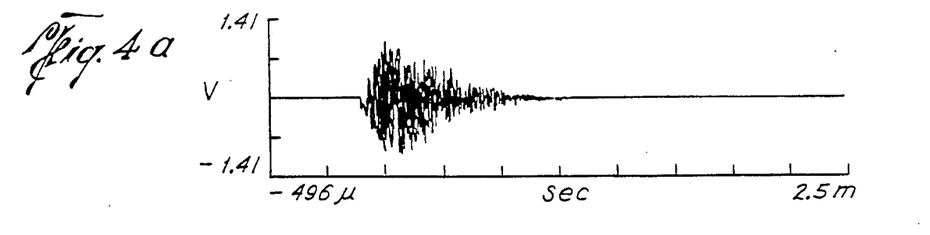
FIG. 4a is a graph illustrating the magnitude and corresponding time in which transmitted surface waves are received upon first receiver of the present invention preferred embodiment.
Figure 4B:
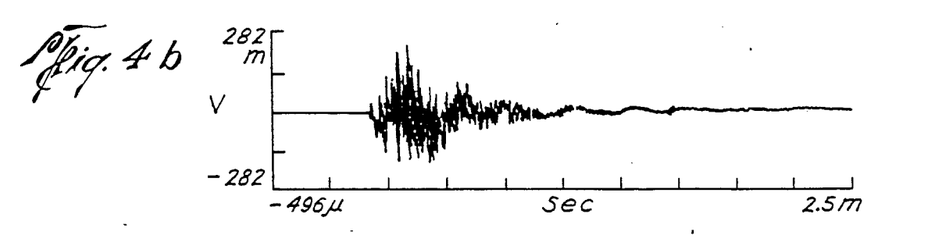
FIG. 4b is a graph illustrating the magnitude and corresponding time in which transmitted surface waves are received by a second receiver of the present invention preferred embodiment.
Figure 4C:
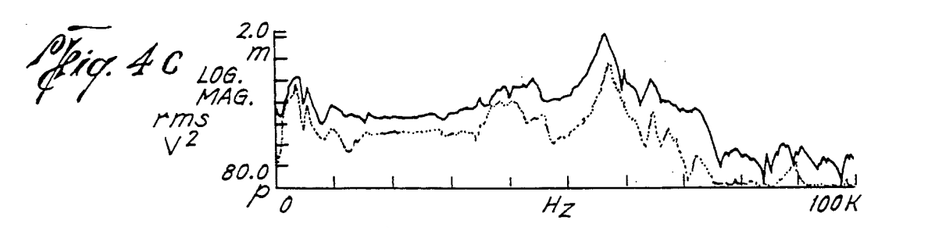
FIG. 4c is a graph illustrating the comparison between voltage magnitudes at various frequencies by first and second receivers of the present invention.

If the distance D between receiver 14A and 14B is set at one foot and $d_2$ is two feet, representative time/amplitude graphs recorded at receivers 14A and 14B are shown in FIGS. 4a and 4b, respectively. Transmitted surface waves are received at receiver 14A slightly before those waves are received on receiver 14B. The time records of FIGS. 4a and 4b are characterized by an initial quiet period followed by an arrival of surface waves (in this preferred example, seismic waves range between a few KHz to approximately 70 KHz). FIGS. 4a–4e are all taken from surface waves transmitted through asphalt concrete after the concrete is fully cured. Piezoelectric generator of the preferred embodiment is used to generate the broad frequency range illustrated. FIG. 4c indicates the distribution of surface wave energy with frequency. Surface wave energy received upon first receiver 14A is indicated by a solid line and surface wave energy received upon second receiver 14B is indicated by a dashed line. As would be expected, the surface wave energy along a broad frequency spectrum is higher at the receiver nearest generator 12 (i.e. first receiver 14A).

The diminution in surface wave amplitude is a natural occurrence of damping or attenuation effects found in curing or cured materials. As FIG. 4c illustrates, attenuation effects are inherent in asphalt concrete. Provided there are no void or anomalies within the concrete, attenuation remains relatively constant throughout the surface of material 20. If attenuation increases or decreases, such that differences in received surface waves increase or decrease, then anomalies exist beneath generator 12 and receiver 14a and 14b. Detecting anomalies is only one of the many useful end results of measuring surface wave attenuation or dampening within material 20.

Figure 4D:
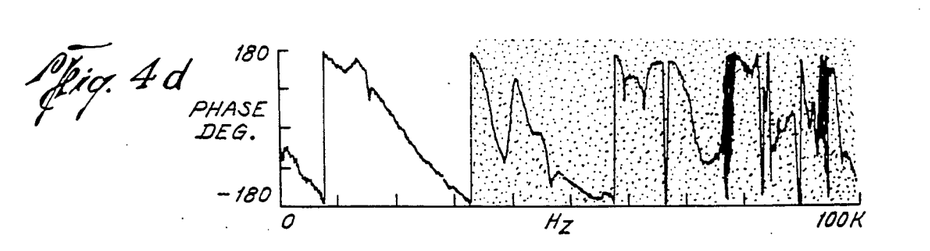
FIG. 4d is a graph illustrating wrapped phase angle shift between signals received by a first and second receiver at various frequencies of the transmitted surface waves.
Figure 4E:
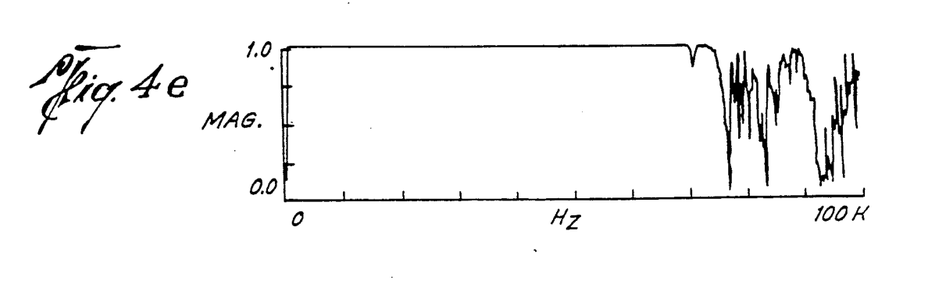
FIG. 4e is a graph illustrating signal-to-noise ratio of the surface wave signals received by first and second receivers.

Cross power spectrum, shown in FIG. 4d, provides the information necessary to calculate the surface wave dispersion curve using the formulas outlined previously. Since travel time is a function of phase angle difference and frequency f, surface wave velocity is determinable from the phase of the cross power spectrum curve shown in FIG. 4d. Surface wave phase velocity can be obtained from cross power spectrum region that is not darkened. The darkened area, corresponding to higher frequencies, is generally contaminated by spurious reflections (35 KHz to 70 KHz) or is unacceptable because sufficient surface wave energy has not been detected (70 KHz to 100 KHz). FIG. 4e illustrates signal-to-noise ratio and the corresponding quality of the received signals. A magnitude of one indicates a strong signal-to-noise ratio, whereas magnitudes sufficiently less than one indicate spurious reflections or unacceptable surface wave energy. Thus, to obtain more accurate surface wave velocity calculations, the phase angle region having low signal-to-noise ratio (i.e. darkened area in FIG. 4d) is filtered out from the resulting dispersion computation. A simple low pass filter with pass band below approximately 40 KHz would be suitable to filter out the darkened areas.

Figure 5:
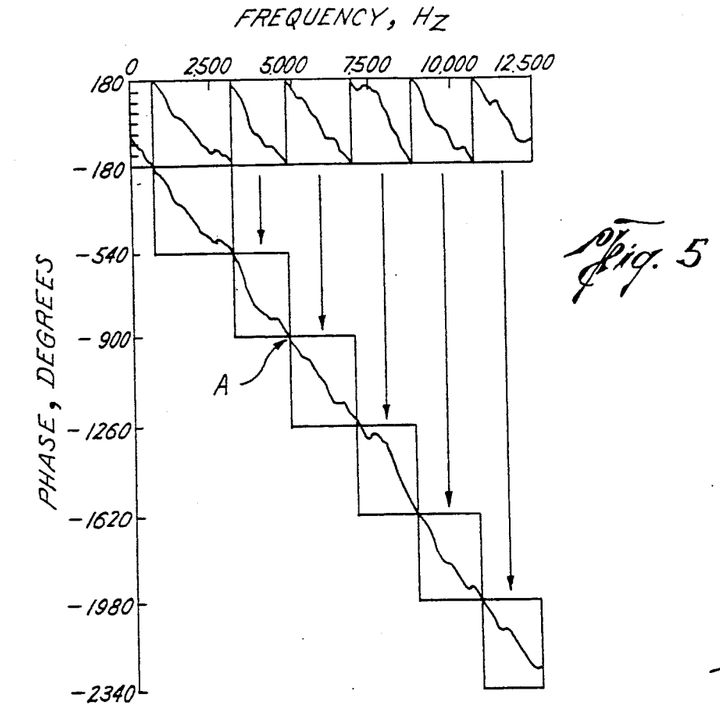
FIG. 5 is a graph illustrating unwrapped phase angle shift between signals received by first and second receivers.

The phase of the cross power spectrum, shown in FIG. 4d, is "wrapped" since the phase value is shown as ranging between −180° to 180°. It is necessary to "unwrap" the phase prior to calculating the dispersion curve. The unwrapped phase of the cross power spectrum is shown in FIG. 5. The phase difference between receiver 14A and receiver 14B is shown along the Y-axis while surface wave frequency is plotted along the X-axis. The phase angle difference and corresponding surface wave frequency allow calculations of travel time between signals detected at the two receivers. For example, if surface wave frequency is transmitted at 5 KHz, then the surface wave phase angles on receiver 14A and 14B must differ by 920°, as shown by point A in FIG. 5. Using phase angle of 920° and frequency of 5 KHz in the travel time formula $$t(f) = \theta yx(f)/2\pi f$$

previously disclosed, travel time is calculated at 0.51 milliseconds (ms). If distance D, is one foot, then surface wave phase velocity, $V_R$, is 1957 feet per second (FPS). By repeating this calculation for every frequency having wavelengths which do not exceed the thickness of the material 20, surface wave phase velocity corresponding to each wavelength (frequency) can be evaluated and a dispersion curve can be determined. As shown in the dispersion curve of FIG. 2, surface wave phase velocity, $V_R$, is substantially constant within the spectrum of wavelengths that do not exceed the thickness of a structurally uniform layer. FIG. 3a illustrates a surface wave phase velocity that changes at the boundaries between structurally uniform layers. Thus, dispersion curves are characterized by an initial constant value over a range of wavelengths corresponding to a structurally uniform layer, with small fluctuations within this range caused by wave reflections within material 20. Small fluctuations, generally less than 10% of the average surface wave phase velocity, are filtered out and discarded such that velocity curves nearly void of spurious fluctuations are obtained as shown in FIGS. 2, 3a and 3b. SASW methods require short wavelengths propagation only within the surface layer. Surface waves with wavelengths greater than, for example, 6-7 inches, sample the pavement layers beneath the surface layer in addition to the surface layer. Large fluctuation in a dispersion curve at wavelengths greater than 11-12 inches are often a result of reflections within material 20, but are of no concern because, all test points are calculated using only the short-wave length test waves (less than 6-7 inches in, for example, asphalt concrete having a surface layer of 8 inches).

Voids residing within the subsurface of material 20, are detectable from dispersion curve 22 or the surface wave phase velocity curve. Changes in surface wave of phase velocity begin to occur at the boundary between non-uniform materials 26A and 26B as shown in FIG. 3a, and also, at points where material 20 is absent (i.e., voids). Regardless of the transmission frequency, surface waves which encounter a void change from a substantially constant surface wave phase velocity to a substantially non-constant surface wave velocity. If surface wave velocity changes or fluctuates more than 25% of the substantially constant surface velocity or if sawtooth phase pattern shown in FIGS. 4d and 5 is substantially disrupted, one is able to detect the presence of one or more voids residing within the subsurface of material 20. Rapid fluctuations, or noisy signals affecting surface wave phase velocity are caused by reflections from the sides of the void or air-pocket walls or from the sides of the anomality. Also, surface wave phase velocity is inherently different within an air pocket than it is through dense material 20. When receivers 14A and 14B surround, or are placed above a subsurface void, surface wave phase velocity between the receivers will demonstrate rapid and substantial fluctuations which indicate to the operator that a subsurface void is present below and between receivers 14A and 14B. If only one receiver is used, voids can be detected below and between generator 12 and the single receiver in the same manner as they are detectable below and between two or more receivers.

The process of finding the strength of the curing or cured material 20, comprises a series of mathematical calculations. The process begins by computing a modulus profile using dispersion curve 22. Calculations of the modulus profile of the present invention are fairly simple and do not require complicated Haskell-Thomson matrix inversion algorithms of prior art. Once the substantially constant wave velocity $V_R$, is found, Young's modulus, or stiffness and strength is calculated from the following formulas:

$$V_S = C \cdot V_R$$

$$G = (w/g) \cdot V_S^2$$

$$E = 2G(1+v)$$

where, $S_{max} = K \cdot G(1+v)$
$C = 1.35 - 0.182 \cdot v$ (for $V \geq 0.1$)
G = Shear modulus,
w = unit weight,
g = acceleration due to gravity,
E = Young's modulus,
$S_{max}$ = strength, and
K = empherical strength factor relating to material type and curing behavior To calculate stiffness, or Young's modulus, of the top pavement layer of cured concrete, Poisson's ratio for concrete is approximately 0.25 and total unit weight, is 145 pounds per cubic foot. Therefore, if for example, surface wave phase velocity, $V_R = 7800$ feet per second, than stiffness or Young's modulus, E, = 5.65 times 10 to the sixth power of PSI. To calculate $S_{max}$, correlations between seismic and laboratory measurements show K equal to 0.002 for modulus in strength in psi. Therefore, comprehensive strength equals 5700 psi for $V_R$ equal to 7800 FPS. Strength factor, K, varies with time and the type of material being tested. At a specific time during the compression testing of a curing material, strength factor K is constant. Laboratory testing using standard compression test will provide the value for K for different types of material and at various curing times. K is 0.002 for relatively dry concrete cement.

Figure 6:
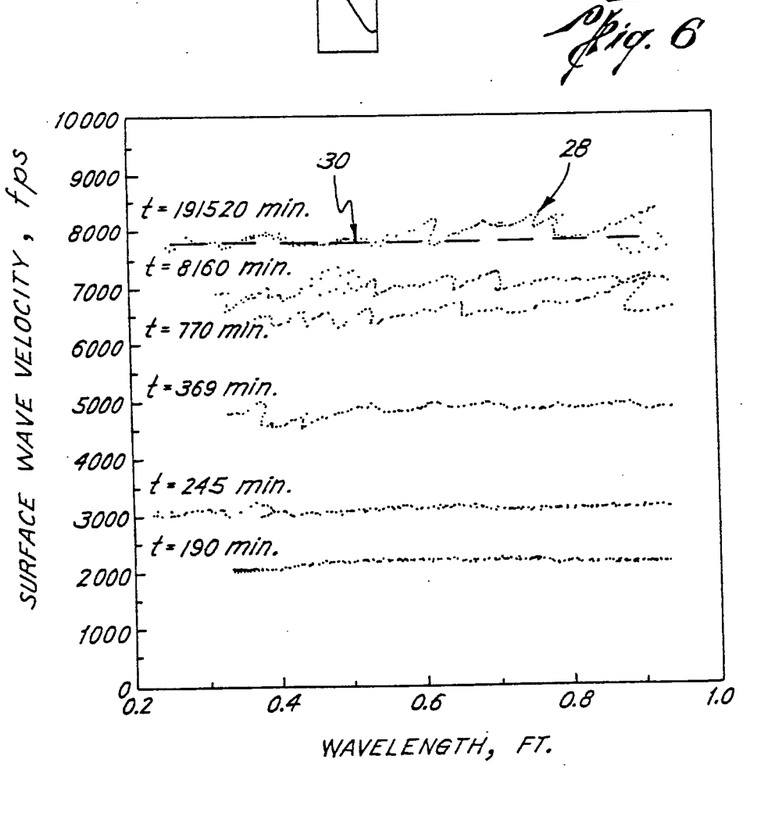
FIG. 6 is a graph illustrating changes in surface wave velocity along the surface of an unreinforced concrete slab at various times during the curing process.

Referring to FIG. 6, surface wave phase velocity in curing Portland cement concrete is shown increasing as the concrete hardens. Measurements taken 190 minutes after water is added to the concrete mix demonstrate that surface wave phase velocity is substantially constant at approximately 2200 feet per second. However, after 191,520 minutes have expired, surface wave phase velocity is less constant but averages around 7800 feet per second. As the concrete hardens, FIG. 6 illustrates that surface wave velocity fluctuations appear more frequently. The fluctuations are caused by reflections from the surface of the hardened concrete, similar to those reflections found off walls of voids or edges and between subsurface layers. Nevertheless, fluctuations 28 shown in FIG. 6 can be filtered or averaged to provide a substantially constant wave velocity line 30. The fluctuations can be filtered or windowed in either the time domain before Fourier Transform or in the frequency domain after Fourier Transform. By windowing the received signals in time domain during time in which energy is incident upon the receivers 14A and 14B, non-direct energy or fluctuations caused by reflected waves can be filtered out leaving a substantially constant wave velocity line 30 instead of fluctuations 28. Because surface wave velocities are inherently more constant in fresh concrete than in hardened concrete, detection of voids, and corresponding fluctuations found in voids, are more apparent in wet concrete than in cured concrete. Thus, voids can be detected during the early curing stages allowing removal of the defective concrete before the concrete has hardened. Also, as demonstrated in FIG. 6, surface wave velocity quickly reaches a high point after which further curing will not substantially increase the velocity. The high velocity point can be easily calculated by waveform analyzer 16 and micro computer 18 such that structural integrity, i.e., strength and modulus of attenuation, can be rapidly determined. Strength is proportional to the maximum Young's modulus, and maximum Young's modulus is proportional to maximum surface wave velocity occurring at a certain time in which material 20 has significantly cured. Therefore, strength of material 20 is proportional to maximum surface wave velocity, however, strength is proportionally dissimilar from Young's modulus or stiffness. Because the values of Young's modulus calculated in the above equations are a result of size measurements, these values represent modulus at very small strain amplitudes. Resulting moduli are therefore maximum values.

Figure 7:
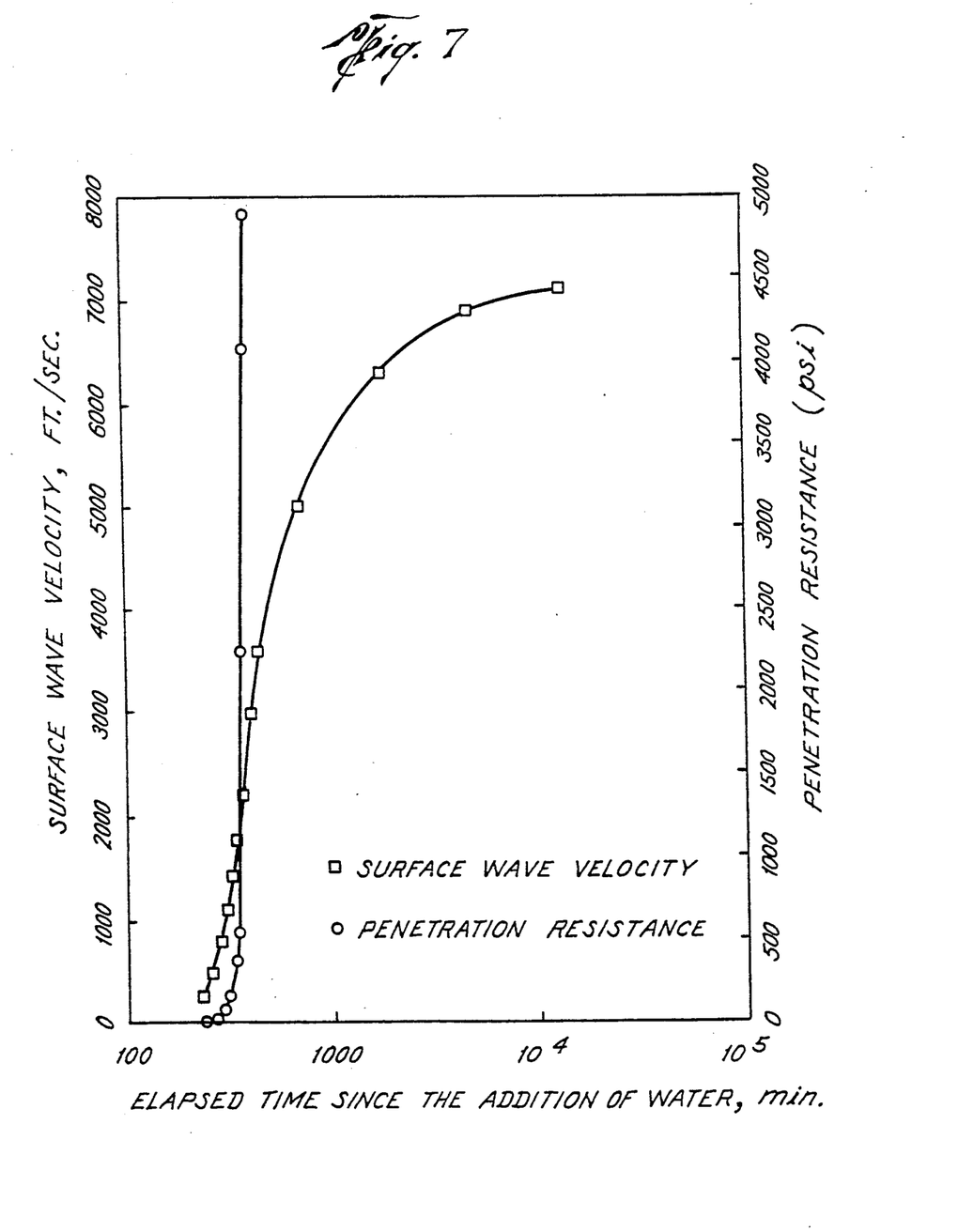
FIG. 7 is a graph comparing surface wave velocity and penetration resistance at various times during the curing process.

Also inherent in the computations is a method of determining penetration resistance, or set time, not at a high level of surface wave velocity used in calculating structural integrity/strength, but rather by the slope of surface wave velocity curve. As discussed in the previous paragraph, surface wave velocity increases as concrete cures but only to a maximum point. Thereafter, surface wave velocity begins to level off to a maximum value as the concrete hardens and is more resistant to penetration tests. FIG. 7 illustrates surface wave velocity, which increases rapidly up to a maximum point. The line having "+" points indicates surface wave velocity, while the line having "0" points in FIG. 7 illustrates conventional penetration resistance test using a standard penetrometer. Comparisons between the two curves indicate that both curves have a fairly equal upward slope at curing times less than 500 minutes after the addition of water. Thus, one can determine penetration resistance from the seismically determined surface wave phase velocity curve instead of the more intrusive penetration method. More importantly, once penetration resistance is found, set time can be determined. Set time being defined as the time it takes for concrete to harden such that penetration test rods (or penetrometers) do not extend more than one inch into the curing concrete as force is being exerted onto the penetrometer. As the concrete cures, more force is needed on the penetrometer in order for it to penetrate into the curing material the necessary one inch distance. Set time is an important attribute of curing concrete which tells the engineers when the concrete can be finished, sawed or walked upon. The present invention does not require a penetrometer to determine penetration resistance. Increased penetration resistance is determined seismically, from the slope of the surface wave velocity curve. Recognizing that a certain surface wave velocity can be extrapolated to a certain penetration resistance, penetration resistance can be computed at various times during the curing process.

The instant invention has been disclosed in connection with specific embodiments. However, it will be apparent to those skilled in the art that variations from the illustrated embodiments may be undertaken without departing from the spirit or scope of the invention. For example, instead of using two receivers, any number of receivers may be used, including one. Also, one or more generators may also be used in conjunction with one or more receivers. Additionally, generator 12 and receivers 14A and 14B are contacted with the exposed surface in material 20 by any method that provides accurate seismic transmission and reception to and from material 20. Furthermore, while most of the studies have been done on curing concrete, this invention is not limited to concrete or curing materials. The method presented herein can be used on any material receptive to seismic waves and surface waves in particular. Therefore, it is the applicant's intentions in the following claims to cover all such equivalent modifications and variations which fall within the true spirit and scope of the invention.

What is claimed is:

1. A method for seismically determining strength of pavement and detecting the presence of voids within the subsurface of the pavement, comprising the steps of:
   seismically contacting at least one surface wave generator with a surface of said pavement;
   seismically contacting at least one receiver with the surface of said pavement a predetermined distance from said generator;
   transmitting surface seismic waves of a plurality of wavelengths along the surface of said pavement from said wave generator to said at least one receiver;
   determining a travel time required for said surface waves to travel between said wave generator and said at least one receiver;
   computing a dispersion curve of surface wave velocity as a function of wavelength by dividing said predetermined distance by said travel time over a range of transmitted wavelengths which do not exceed a thickness of said pavement;
   determining a strength of said pavement by multiplying an empirical strength factor by said substantially constant surface wave velocity; and,
   detecting voids in said pavement by localizing pavement areas through which surface waves are transmitted which cause said surface wave velocity to change from a substantially constant velocity to a substantially non-constant velocity.

2. A method for seismically determining strength of a paved surface and for detecting the presence of voids beneath the paved surface, comprising the steps of:
   contacting at least one surface wave generator with said paved surface;
   contacting at least two receivers upon said paved surface a predetermined distance apart, whereby one of said at least two receivers is nearer said generator than others of said at least two receivers;
   transmitting surface waves at varying frequencies from said generator to said receivers;
   measuring a travel time required for said surface waves to travel between said receivers at each surface wave frequency;
   computing a dispersion curve of surface wave velocity as a function of wavelength by dividing said predetermined distance by said travel time over a spectrum of frequencies having wavelengths which do not exceed the thickness of said paved surface;
   determining a strength of said pavement by multiplying a strength factor by said surface wave velocity for constant values of said velocity; and,
   detecting voids in said pavement by localizing pavement areas, through which surface waves are transmitted, which cause said surface wave velocity to change from a substantially constant velocity to a substantially non-constant velocity.

3. The method according to claim 2, wherein said surface wave generator produces surface seismic waves transmitted through said paved surface having frequencies ranging from 1 KHz to 100 KHz.

4. The method according to claim 2, wherein said first and second receivers produce electric signals in response to surface seismic waves transmitted through said paved surface.

5. A device for determining subsurface anomalies, strength, thickness, set time and attenuation modulus of materials having structural properties that change with time, comprising:
   at least one surface wave generator seismically connected to an exposed surface of said material for generating surface waves within a surface region of said material;
   at least one surface wave receiver seismically connected to an exposed surface a known distance from said wave generator for receiving surface waves within the surface region of said material;
   a waveform analyzer electrically connected to said receivers for measuring a travel time required for said surface waves to travel said known distance along the surface region of said material;
   a micro computer electrically connected to said waveform analyzer with means for computing:
      a surface wave velocity by dividing said known distance by said travel time;
      subsurface anomaly location by detecting substantial fluctuation in said surface wave velocity as a function of wavelengths of said surface waves;
      strength of said material by multiplying a strength factor by said surface wave velocity as a function of time;
      thickness of said material by determining a wavelength of said surface wave corresponding to said thickness that causes said surface wave velocity to change from a substantially constant value to a substantially non-constant value;
      set time of said material during which said material are being cured by determining the set time as a function of said surface wave velocity at various times during curing; and,
      attenuation modulus of said material by computing differences in amplitude of said surface waves at a plurality of known distances from said generator.

* * * * *